US007060299B2

(12) United States Patent
Alavattam et al.

(10) Patent No.: US 7,060,299 B2
(45) Date of Patent: Jun. 13, 2006

(54) BIODEGRADABLE MICROPARTICLES THAT STABILIZE AND CONTROL THE RELEASE OF PROTEINS

(75) Inventors: Sreedhara Alavattam, Columbus, OH (US); Richard S. Brody, Worthington, OH (US)

(73) Assignee: Battelle Memorial Institute, Columbus, OH (US)

( * ) Notice: Subject to any disclaimer, the term of this patent is extended or adjusted under 35 U.S.C. 154(b) by 112 days.

(21) Appl. No.: 10/750,475

(22) Filed: Dec. 31, 2003

(65) Prior Publication Data

US 2004/0175429 A1 Sep. 9, 2004

Related U.S. Application Data

(60) Provisional application No. 60/486,842, filed on Jul. 11, 2003, provisional application No. 60/437,351, filed on Dec. 31, 2002.

(51) Int. Cl.
*A61K 9/64* (2006.01)
*A61K 9/22* (2006.01)
*A61K 9/14* (2006.01)

(52) U.S. Cl. ............... 424/491; 424/468; 424/485; 424/486; 424/488; 530/421

(58) Field of Classification Search ............... 530/421; 424/486, 485, 488, 468
See application file for complete search history.

(56) References Cited

U.S. PATENT DOCUMENTS

| 3,773,919 A | 11/1973 | Boswell et al. |
| 3,887,699 A | 6/1975 | Yolles |
| 4,293,539 A | 10/1981 | Supcoe et al. |
| 4,675,189 A | 6/1987 | Kent et al. |
| 5,700,486 A | 12/1997 | Canal et al. |
| 5,759,583 A | 6/1998 | Iwamoto et al. |
| 5,981,719 A | 11/1999 | Woiszwillo et al. |
| 5,985,309 A | 11/1999 | Edwards et al. |
| 6,120,787 A | 9/2000 | Gustafsson et al. |
| 6,238,705 B1 | 5/2001 | Liu et al. |
| 6,294,202 B1 | 9/2001 | Burns et al. |
| 6,391,296 B1 | 5/2002 | Okano et al. |
| 6,896,894 B1 * | 5/2005 | Brody et al. ............... 424/425 |

FOREIGN PATENT DOCUMENTS

| EP | 0 950 663 A1 | 10/1999 |
| WO | WO 02/28370 A1 | 4/2002 |

OTHER PUBLICATIONS

Stabilization of proteins encapsulated in injectable poly(lactide-co-glycolide). Gaozhong Zhu, Susan R. Mallery, and Steven P. Schwendeman. Nature Biotechnology. 2001: 18:52-57.*

Erythropoietin loaded microspheres prepared from biodegradable LPLG-PEO-LPLG triblock copolymers: protein stabilization and in-vitro release properties. Morlock M, Kissel T, Li YX, Koll H, Winter G. J. Controlled Release. 1998: 56: 105-115.*
Concentration and fractionation of polyvinyl alcohol-anionic surfactant stabilised latex dispersions by microfiltration. R.J. Wakeman *, G. Akay. 1995. J. Membrane Science. 106:57-65.*
Austin et al.; The Controlled Release of Leukaemia Inhibitory Factor (LIF) From Aliginate Gels; Pro Intern Symp Control Rel Bioact Mater; 23; 1996; pp. 739-740.
Brannon-Peppas et al.; Polyactic and Polyglycolic Acids as Drug Delivery Carriers; Handbook of Pharmaceutical Release Tech; 2000; pp. 99-130; Marcel Dekker; New York.
Burgess et al.; Glucuronidase Activity Following Complex Coacervation & Spray Drying Micoencapsulation; J. Microencapsulation; 1998; vol. 15; No. 5; pp. 569-579.
Burke, Paul; Controlled Relase Protein Therapeutics: Effects of Process & Formulation on Stability; Handbook of Pharmaceutical Controlled Release Tech; 2000; pp. 661-692.
Chang, Thomas; Biodegradable Semipermeable Microcapsules Containing Enzymes Hormones Vaccines & Other Biologicals; J of Bioengineering; 1976; vol. 1; pp. 25-32.
Chen et al. Polysaccharide Hydrogels for Protein Drug Delivery; Carbohydrate Polymers 28; 1995; pp. 69-76; Elsevier; Great Britain.
Cleland et al.; Stable Formulations of Recombinant Human Growth Hormone & Interferon-for Microencapsulation in Biodegradable Microspheres; Pharmaceutical Research; vol. 13; No. 10; 1996; pp. 1464-1475.
Crotts et al. Protein Delivery From Poly(lactic-co-glycolic acid) Biodegradable Microspheres: Release Kinetics & Stability Issues; J Microencapsulation 1998; 15; 6; pp. 699-713.
De Rosa et al; Influence of Co-encapsulation of Different Non-Ionic Surfactants on the Properties of PLGA Insulin-loaded Microspheres; J Controlled Release 69 2000 pp. 283-295.
Gombotz et al.; Protein Release From Alginate Matrices; Advanced Drug Delivery Reviews; 31; 1998; pp. 267-285; Elsevier.
Huang et al.; On The Importance & Mechanismsof Burst Release in Matrix-controlled Drug elivery Systems; J of Controlled Release; 73; 2001; pp. 121-136; Elsevier.

(Continued)

*Primary Examiner*—Robert A. Wax
(74) *Attorney, Agent, or Firm*—Klaus H. Wiesmann

(57) ABSTRACT

Disclosed herein are biodegradable microparticle compositions, and methods for the generation of biodegradable and biocompatible microparticles that stabilize proteins and also control the kinetics of release of proteins over a period of several weeks to several months under physiological conditions.

27 Claims, 6 Drawing Sheets

OTHER PUBLICATIONS

Jain et al.; Controlled Drug Delivery by Biodegradable Poly(Ester) Devices: Different Preparative Approaches; Drug Development & Industrial Pharmacy; 1998; vol. 24; pp. 703-727.

Jiang et al.; Stabilization & Controlled Release of Bovine Serum Albumin Encapsulated in Poly(D, L-lactide) and Poly(ethylene glycol) Microsphere Blends; Pharmaceutical Research; vol. 18; 6; 2001; pp. 878-885.

Johansen et al; Improving Stability & Release Kinetics of Microencapsulated Tetanus Toxoid by Co-Encapsulation of Additives; Pharmaceutical Reseach vol. 15; 7 1998 pp. 1103-1110.

Lee et al.; Double Walled Microparticles For HBV Single Shot Vaccine; Proceed Intern Symp Control Rel Bioact Mater; 23; 1996; pp. 333-334; #4103; Controlled Release Soc.

Li et al.; A Novel Biodegradable System Based on Gelatin Nanoparticles and Poly(lactic-co-gylcolic acid) Microspheres for Protein and Peptide Drug Delivery; J Pharmaceutical Sciences; vol. 86; No. 8; Aug. 1997; pp. 891-895.

Park et al.; Poly(L-lactic acid) Pluronic Blends: Characterization of Phase Separation Behavior, Degradation and Morphology and Use as Protein-Releasing Matrices; Macromolecules; 1992; 25; pp. 116-122; American Chemical Society.

Patil et al.; Water-Based Microsphere Delivery System for Proteins; J of Pharmaceutical Sciences; vol. 89; No. 1; Jan. 2000; pp. 9-15.

Pean et al.; Why Does PEG 400 Co-Encapsulation Improve NGF Stability & Release From PLGA Biodegradable Microspheres; Pharmaceutical Research; vol. 16; No. 8; 1999; pp. 1294-1299.

Prokop et al.; Water Soluble Polymers for Immunoisolation II: Evaluation of Multicomponent Microencapsulation Systems; Advances in Polymer Science; vol. 136; pp. 53-73; 1998.

Putney et al.; Encapsulation of Proteins for Improved Delivery; Current Opinion In Chemical Biology; 1998; 2 pp. 548-552.

Roskos et al.; Degradable Controlled Release Systems Useful for Protein Delivery; Protein Delivery: Physical Systems, Sanders & Hendren eds.; Plenum Press; NY; pp. 45-92; 1997.

Sanchez et al.; Formulation Strategies for Stabilization of Tetanus Toxoid in Poly (lactide-co-glycolide) Microspheres; Inter J of Pharmaceutics; 185; 1999 pp. 255-266; Elsevier.

Sandor et al.; Effect of Protein Molecular Weight on Release From Micro-Sized PLGA Micoospheres; J of Controlled Release; 76; 2001; pp. 297-311; Elsevier.

Sezer et al.; Release Characteristics of Chitosan Treated Alginate Beads: I. Susteained Release of a Macromolecular Drug From Chitosan Treated Alginate Beads; J Microencapsulation; 1999; vol. 16; No. 2; pp. 195-203.

Van De Weert et al.; Protein Instability in Poly(Lactic-co-Glycolic Acid) Microparticles; Pharnaceutical Research; vol. 17; No. 10; 2000; pp. 1159-1167.

Wang et al.; A heterogenously Structured Composite Based on Poly(lactic-co-glycolic acid) Microspheres and Poly (vinyl alcohol) Hydrogel Nanoparticles for Long-Term Protein Drug Delivery; Pharmaceutical Research; vol. 16; No. 9; 1999; pp. 1430-1435.

Wang et al.; A Novel Approach to Stabilization of Protein Drugs in Poly(lactic-co-glycolic acid)microspheres Using Agarose Hydrogel; Inernational Journal of Pharmaceutics; 166; 1998; pp. 1-14.

Wheatley et al.; Coated Alginate Microspheres: Factors Influencing the Controlled Deliery of Macromolecules; J of Applied Polymer Science; vol. 43; pp. 2123-2135; 1991.

Woo et al.; Preparation adn Characterization of a Composite PLGA and Poly(Acrylol Hydroxyethyl Starch) Microsphere System for Protein Delivery; Pharmaceutical Research; vol. 18; No. 11; Nov. 1002; pp. 1600-1606.

* cited by examiner

BIODEGRADABLE MICROPARTICLES THAT STABILIZE AND CONTROL THE RELEASE OF PROTEINS

This application claims the benefit of Provisional Application Ser. No. 60/437,351 filed Dec. 31, 2002, and of Provisional Application Ser. No. 60/486,842 filed Jul. 11, 2003.

TECHNICAL FIELD

Described herein are methods for the generation of biodegradable and biocompatible microparticles that contain stabilized proteins and also control the kinetics of release of proteins over a period of several weeks under physiological conditions. Specifically, novel methods to make stable protein microparticles encapsulated in hydrophobic biodegradable carriers such as poly(lactic-co-glycolic) acid polymers are described. Typically, the present invention provides for a formulation that controls an initial burst of the protein from PLGA microspheres, in some embodiments shows almost complete release of protein (about 80% of encapsulated protein is released after 28 days) and can release the protein in a near linear fashion over a period of about one month.

BACKGROUND OF THE INVENTION

Copolymers containing lactic acid and glycolic acid residues (poly(lactic acid-co-glycolic acid) or PLGA) have been used for sutures, structural implants, and as drug delivery vehicles since the 1970s. The use of these biodegradable polymers for drug delivery is reviewed by Brannon-Peppas, L. and Vert, M. "Polylactic and Polyglycolic Acids as Drug Delivery Carriers" in Handbook of Pharmaceutical Controlled Release Technology, Wise, D. L. ed., Marcel Dekker, New York, pp. 99–130, 2000. The preparation of PLGA polymers for drug delivery applications by methods such as single emulsion, double emulsion, phase separation, and spray drying is reviewed by Jain et al., Drug Development and Industrial Pharmacy, Vol. 24, pp 703–727, 1998. Examples of early work on the use of PLGA prepare films and to prepare spray dried particles were described in U.S. Pat. Nos. 3,773,919, 3,887,699, and 4,293,339 and examples of early work on the preparation of polylactic acid or PLGA microcapsules for the release of biologically active compounds were described in T. Chang, J. Bioeng., Vol 1, pp 25–32, 1976 and in U.S. Pat. No. 4,675,189.

The incorporation of proteins into PLGA microparticles and the release profiles of these proteins from the microparticles into physiological solutions has been intensively investigated, as reviewed by Roskos, K. V. and Maskiewicz, R. "Degradable Controlled Release Systems Useful for Protein Delivery" in Protein Delivery: Physical Systems, Sanders and Hendren eds., Plenum press, New York, pp. 45–92, 1997 and Putney, S. D., Current Opinion in Chemical Biology, Vol 2, pp 548–552, 1998.

Major problems associated with the release of protein therapeutics from biodegradable PLGA particles include the stability of the protein, both during incorporation in the PLGA particle and during release (reviewed by van de Weert et al., Pharmaceutical Research, Vol 17, pp. 1159–1167, 2000 and Burke, P. "Controlled Release Protein Therapeutics: Effects of Process and Formulation on Stability" in Handbook of Pharmaceutical Controlled Release Technology, Wise, D. L. ed., Marcel Dekker, New York, pp. 661–692, 2000), and the ubiquitous presence of a "burst" effect, where a significant fraction of the protein incorporated in the microparticle is released immediately after the particle is introduced into a physiological solution, followed by a much slower rate of long term protein release (reviewed by Crotts, G. and Park, T. G., Journal of Microencapsulation, Vol. 15, pp. 699–713, 1998; Sandor et al., Journal of Controlled Release, Vol. 76, pp. 297–311, 2001; and Huang, X. and Brazel, C. S., Journal of Controlled Release, Vol. 73, pp. 121–136, 2001).

There are many reports in the literature of the use of hydrophilic gels to protect proteins from inactivation during PLGA microsphere formation and to the use of these gels to modify the protein release profile in a physiological solution. The following are examples of protein-loaded gels that researchers have incorporated into PLGA microparticles: gelatin nanoparticles (Li et al., Journal of Pharmaceutical Sciences, Vol. 86, pp. 891–895, 1997), agarose (Wang, N, and Wu, X. S., International Journal of Pharmaceutics, Vol. 166, pp. 1–14, 1998), dextran, heparin, alginate, or bovine serum albumin (Sanchez et al., International Journal of Pharmaceutics, Vol 185, pp. 255–266, 1999), poly(vinyl alcohol) (Wang et al., Pharmaceutical Research, Vol. 16, pp 1430–1435, 1999), Poly(acryloyl hydroxyethyl starch) (Woo et al., Pharmaceutical Research, Vol. 18, pp 1600–1606, 2001), and hydroxypropyl cellulose (Lee et al., Proceed. Intern. Symp. Control. Rel. Bioact. Mater., Vol 23, pp. 333–334, 1996). These literature reports indicate that the use of hydrophilic gels can, in some cases, increase the incorporation of protein into the PLGA particle, increase the stability of the protein in the PLGA particle, and increase the total amount of protein released from the PLGA particle. In no case, however, did addition of the gel prevent the initial burst of protein release that occurred when the particles were suspended in a physiological solution. In many of these cases, the stability of the protein has not been determined.

Neutral surfactants such as Tween (Cleland, J. L. and Jones, A. J. S., Pharmaceutical Research, Vol. 13, pp. 1464–1475, 1996), poly(ethylene glycol) (Pean, J.-M. et al., Pharmaceutical Research, Vol. 16, pp. 1294–1299, 1999), γ-hydroxypropyl cyclodextrin (Johansen, P. et al., Pharmaceutical Research, Vol. 15, pp. 1103–1110, 1998), and polyoxamer (De Rosa et al., Journal of Controlled Release, Vol. 69, pp. 283–295, 2000) have been added to the aqueous protein phase used to make PLGA particles. Surfactants such as Pluronic™ (Park et al., Macromolecules, Vol. 25, pp. 116–122, 1992) and poly(ethylene glycol) (Jiang, W. and Schwendeman, S. P., Pharmaceutical Research, Vol. 18, pp. 878–885. 2001) have been added to the organic PLGA phase during particle preparation. In some cases, the addition of surfactants stabilizes the protein to emulsification processes and increases the total amount of protein released into physiological solution. In no case, however, do these surfactants remove the burst effect or change the release profile so that the amount of protein released into solution is constant over time.

The incorporation of charged surfactants into PLGA particles has been described in U.S. Pat. No. 5,985,309. In this case, the inventors incorporated charged therapeutic agents and surfactants with the opposite charge in their PLGA formulations. Quaternary ammonium surfactants were incorporated into PLGA particles and shown to increase the percentage release for small molecular weight therapeutic agents (U.S. Pat. No. 5,759,583).

Polysaccharide hydrogels have been extensively investigated as possible vehicles for protein delivery, as reviewed by Chen, J. et al., Carbohydrate Polymers, Volume 28, pp. 69–76, 1995. Particles of polysaccharides have been prepared with proteins or small molecular weight drugs and then coated with cationic molecules. For example, alginate particles have been coated with polylysine, poly(ethylene imine) or chitosan (Wheatley et al., Journal of Applied Polymer Science, Vol 43, pp. 2123–2135, 1991; Austin et al., Proceed. Intern. Symp. Control. Rel. Bioact. Mater., Vol 23, pp. 739–740, 1996; Gombotz, W. R. and Wee, S. F., Advanced Drug Delivery Reviews, Vol, 31, pp. 267–285, 1998; Sezer, A. D. and Akbuga, J., J. Microencapsulation, Vol. 16, pp. 195–203, 1999; U.S. Pat. No. 6,238,705 B1) and carrageenan particles have been coated with oligoamines, diamines, and monamines (Patil, R. T. and Speaker, T. J., Journal of Pharmaceutical Sciences, Vol 89, pp. 9–15, 2000). In most cases proteins are released from these particles in hours or days, although longer release times have been proposed. Prokop et al., (Advances in Polymer Science, Vol, 136, pp. 53–73, 1998) report the coating of multiple polysaccharide polyanion blends with multiple polycation blends in order to microencapsulate cells for immuno-isolation. It has been reported that anionic polysaccharide films, foams, and fibers can be spray coated or brush coated with PLGA (U.S. Pat. No. 6,294,202 B1).

The use of gum arabic to stabilize lyophilized protein is described in the European Patent application #EP0950663A1 and in the U.S. Pat. No. 6,391,296 and the use of high gum arabic concentrations to stabilize proteins in solution is described in our U.S. patent application Ser. No. #12988. Complex coacervates have been made from gum arabic and cationic proteins, which have been spray dried to form microparticles (Burgess, D. J. and Ponsart, S., Journal of Microencapsulation, Vol. 15, pp. 569–579, 1998). The enzyme β-glucuronidase was encapsulated in this system in the absence of PLGA. Approximately 30% of the encapsulated enzyme was released in a burst when these particles were added to a physiological buffer and an additional 30% of the enzyme was released with a linear rate over 12 days.

U.S. Pat. No. 6,294,202 describes the compositions of anionic polysaccharides in bioabsorbable polymers. U.S. Pat. No. 5,700,486 describes novel pharmaceutical compositions that are able to overcome the drawbacks of the known art.

In U.S. Pat. No. 5,981,719 generally the polymers form the supporting structure of these microspheres, and the drug of interest is incorporated into the polymer structure.

U.S. Pat. No. 5,759,583: This invention provides a sustained release composition comprising a PLGA matrix, a bioactive agent, and a quaternary ammonium surfactant, in which the release profile of the bioactive agent from the PLGA matrix is controlled by the concentration of the quaternary ammonium surfactant.

U.S. Pat. No. 5,985,309: Particles incorporating a surfactant and/or a hydrophilic or hydrophobic complex of a positively or negatively charged therapeutic agent and a charged molecule of opposite charge for drug delivery to the pulmonary system, and methods for their synthesis and administration are provided.

U.S. Pat. No. 6,120,787 and WO 02/28370 A1: describe the use microparticles of a core material consisting of amylopectin-based starch and a biologically active substance that may be encapsulated with an outer release controlling shell.

In many of the examples from the prior art, there is a substantial initial burst effect, and very little protein released after that. Protein modifications, aggregation and loss of activity are also noticed in many formulations. Thus, given the current state of the art, there is a need for compositions and methods that effectively stabilize a variety of proteins to various physical and chemical environments, reduce the initial burst effects, and substantially release all the encapsulated protein. The present invention provides materials and methods to stabilize proteins, control the initial burst, and release the encapsulated protein in a controlled manner over a period of time.

SUMMARY OF THE INVENTION

The invention broadly includes controlled release formulations comprising a protein mixed with a stabilizer to form a stabilized matrix which is encapsulated in a biodegradable polymer (with or without first being reacted with a surfactant) to form a stabilized microsphere. One typical embodiment discloses the preparation of PLGA microspheres that contain one (or more) smaller particles embedded in a PLGA matrix. The smaller particles typically consist of a therapeutic agent embedded in a charged biopolymer. One novel aspect of this invention is that a biopolymer used to stabilize the protein is a polysaccharide gum that is shown herein to be an effective protein stabilizer at high concentrations and different ratios of protein to gum. The biopolymer and protein typically form stabilized protein particles typically in the from of a matrix. Another novel aspect of this invention is that the stabilized protein particles are coated with detergent molecules whose polar head group contains a charge opposite to that of the stabilized protein. The detergent coating dramatically affects the release profile for the therapeutic agent. In the case of PLGA microspheres that contain an uncoated polysaccharide biopolymer and a protein, or in the case of PLGA microparticles that contain only the protein, most of the protein is typically immediately released into a physiological buffer in an initial burst. When the protein embedded in polysaccharide particles are coated with an oppositely charged molecule, the burst is dramatically reduced and the therapeutic agent is released at a controlled rate for an extended period of time (e.g. weeks).

Typical embodiments of the invention include a controlled release formulation comprising: a protein mixed with a stabilizer and encapsulated in a biodegradable polymer. In some embodiments the protein, stabilizer, and a surfactant are encapsulated in the biodegradable polymer. The biodegradable polymer preferably comprises homo or heteropolymers of lactic and glycolic acids.

In other embodiments biodegradable polymers include hydrophobic bioabsorbable polymers such as polyglycolide, polylactide (D, L, DL), polydioxanones, polyestercarbonates, polyhydroxyalkonates, polycaprolactone (polylactones), polyethylene glycol, mixtures thereof, and copolymers made from two or more precursors of the above. The most preferable polymers are polyglycolide or polylactide, or copolymers selected from two or more precursors of polyglycolide, polycaprolactone, or polylactide.

A further embodiment of the invention includes a controlled release formulation comprising a protein a polysaccharide stabilizer mixed with the protein; and a surfactant coated on the stabilizer protein mixture. Typically the protein and stabilizer are coated with the surfactant. Typically the stabilized protein has a charge and the surfactant has a charge opposite to it. In some cases the stabilized protein is uncharged and the surfactant is uncharged. In other cases the stabilized protein is uncharged and the surfactant is charged.

In a yet further embodiment the invention includes a controlled release formulation comprising a protein a polysaccharide gum stabilizer mixed with the protein; and a biodegradable polymer encapsulating the protein stabilizer mixture. One embodiment includes a method for making stabilized protein particles comprising providing a solution of protein; providing a solution of stabilizer; mixing the solutions; and generating stabilized protein particles from the mixture. Typically the method includes particles that are generated by spray drying, lyophilization, electrohydrodynamic technology, or other methods typical in the art to produce particles from solutions. Typically the stabilizer is selected form the group consisting of polysaccharides, carrier proteins, and mixtures thereof. The polysaccharides are typically chosen from polysaccharide gums not limited to but including, guar gum, gum arabic, gum karaya, gum ghatti, locust bean gum, tamarind gum, carageenan gum, and pectin or mixtures thereof. In some embodiments the stabilizer is a carrier protein, and may be HSA, gelatin, BSA, and mixtures thereof.

Typically the polymers are biodegradable polymers that are selected from a group polymers that are sensitive to environmental physiological conditions (e.g. temperature, pH, moisture). In some embodiments the polymers are block copolymers or graft copolymers.

Another embodiment of the invention includes a method for making stabilized protein particles comprising providing a solution of protein; providing a solution of stabilizer; mixing the solutions; generating stabilized microparticles from the mixture; and if desired coating the microparticles with surfactant. Typically the methods herein provide for a method for producing stabilized protein particles comprising providing source of protein; providing a source of stabilizer; mixing the stabilizer and protein, wherein the ratio of stabilizer to protein is an amount effective for stabilizing the protein. In some embodiments the stabilized protein particles are typically suspended in an organic solvent and coated with a surfactant. Typically the organic solvent is selected from the group consisting of ethanol, dichloromethane, dimethyl sulfoxide, dimethyl formamide and mixtures thereof.

In one embodiment the protein and stabilizer are mixed in a ratio of stabilizer:protein of about 500:1 to about 1:1. In another embodiment the protein and stabilizer are mixed in a ratio of stabilizer:protein of about 10,000:1 to about 50:1. In another embodiment the protein comprises a therapeutic protein, and the protein and stabilizer are mixed in a ratio of stabilizer:protein of about 500:200 to about 1:1. In yet another embodiment the protein comprises a therapeutic protein, the protein and stabilizer are mixed in a ratio of stabilizer:protein of about 100,000:1 to about 1:1. Typically the method provides that the surfactant coated particle that contains protein and stabilizer are encapsulated in a biodegradable polymer.

Typically, the materials of the various embodiments of the invention are formulations provided with biologically effective amounts of a protein and a stabilizing effective amount of a stabilizer.

The various embodiments herein provide for stabilization of the protein to towards handling and treatment such as sonication, homogenization, emulsification, drying, and the like, and combinations of the above.

Typical stabilization periods provide for effective stabilization for at least about 4 weeks. In some embodiments at least about 50% of the protein is stable during release over a period of about at least 3 weeks, and most preferably at least 4 weeks.

DETAILED DESCRIPTION OF THE INVENTION AND BEST MODE

Figure 1:
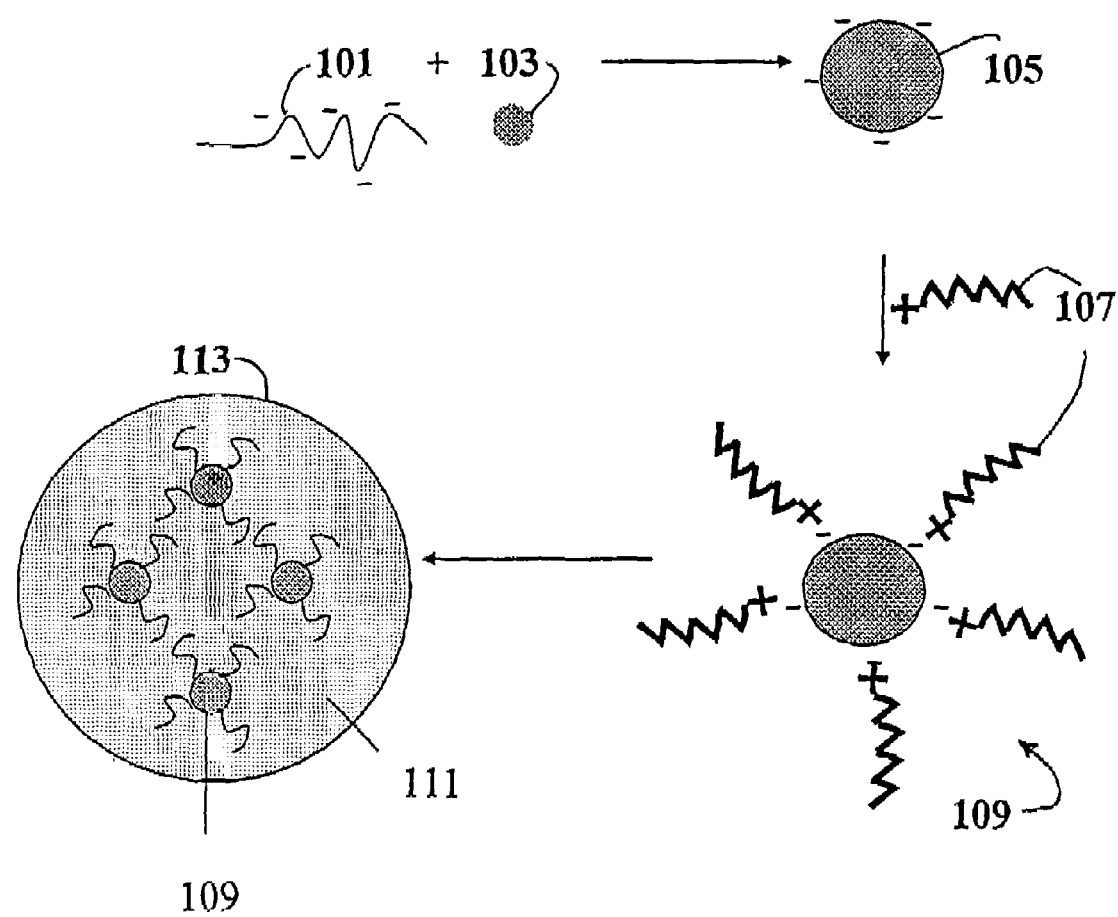
FIG. 1 is a schematic diagram showing the steps in the production of the microparticles according to the invention. The figure illustrates an embodiment utilizing a negatively charged stabilizer.
Figure 2:
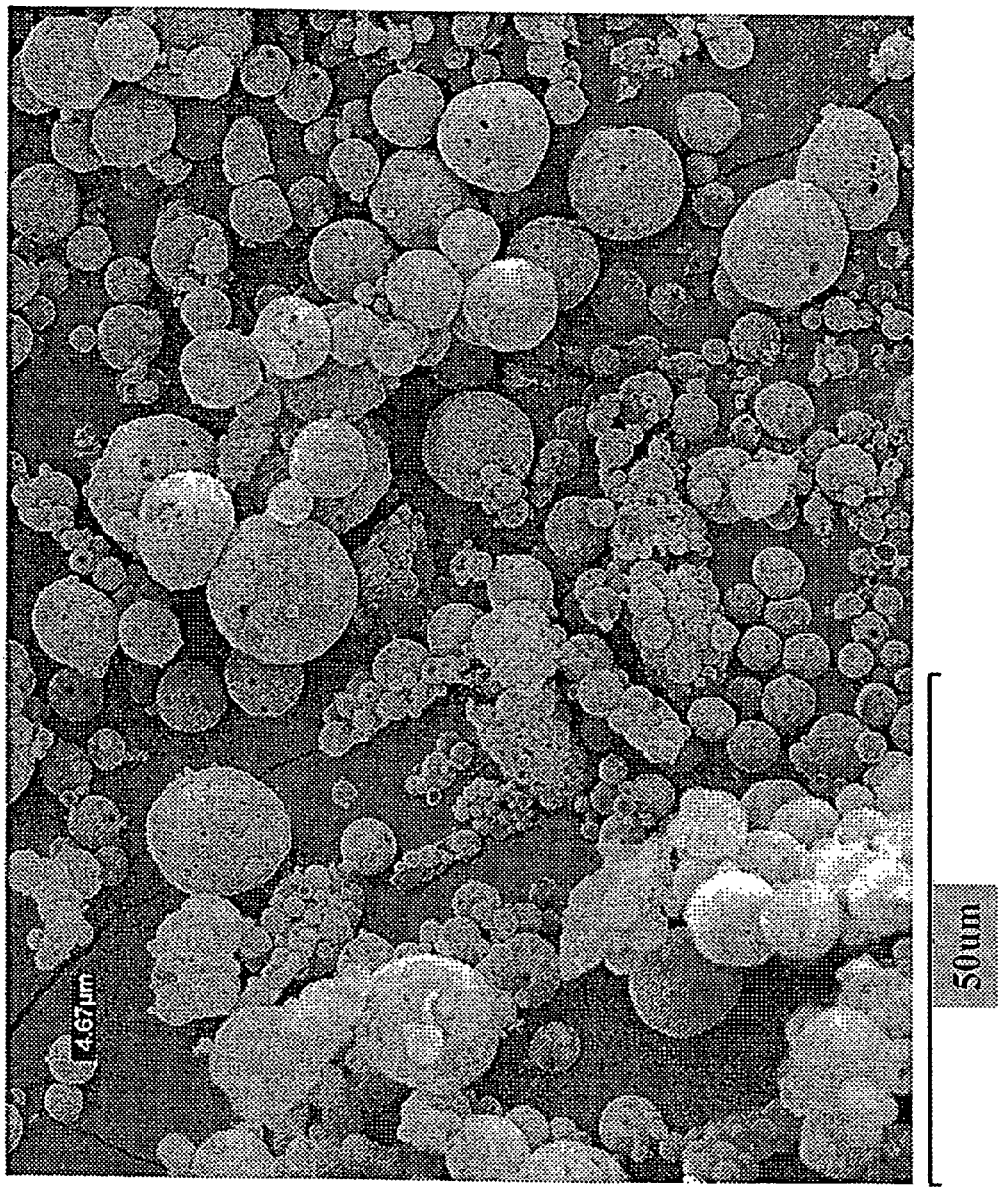
FIG. 2 shows the results of a scanned electron micrograph of stabilized microparticles 105 according to the invention.
Figure 3:
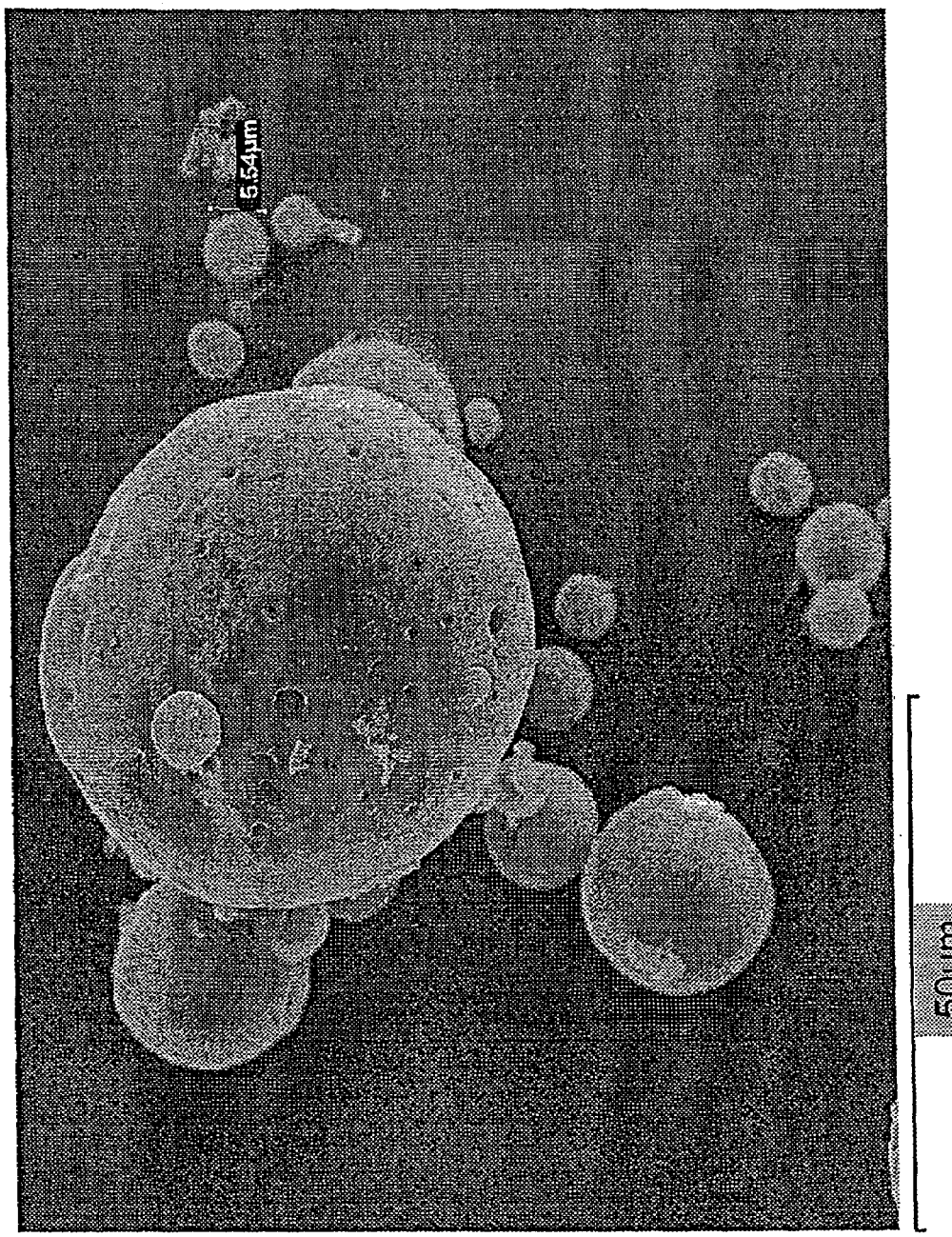
FIG. 3 shows the SEM pictures of the microparticles containing the stabilizer (101) with protein (103) coated with surfactant (107) and encapsulated in PLGA (111).
Figure 4:
FIG. 4 shows the initial burst (24 hours) from microparticles containing stabilizer and protein particles coated with different surfactants and encapsulated in PLGA.
Figure 5:
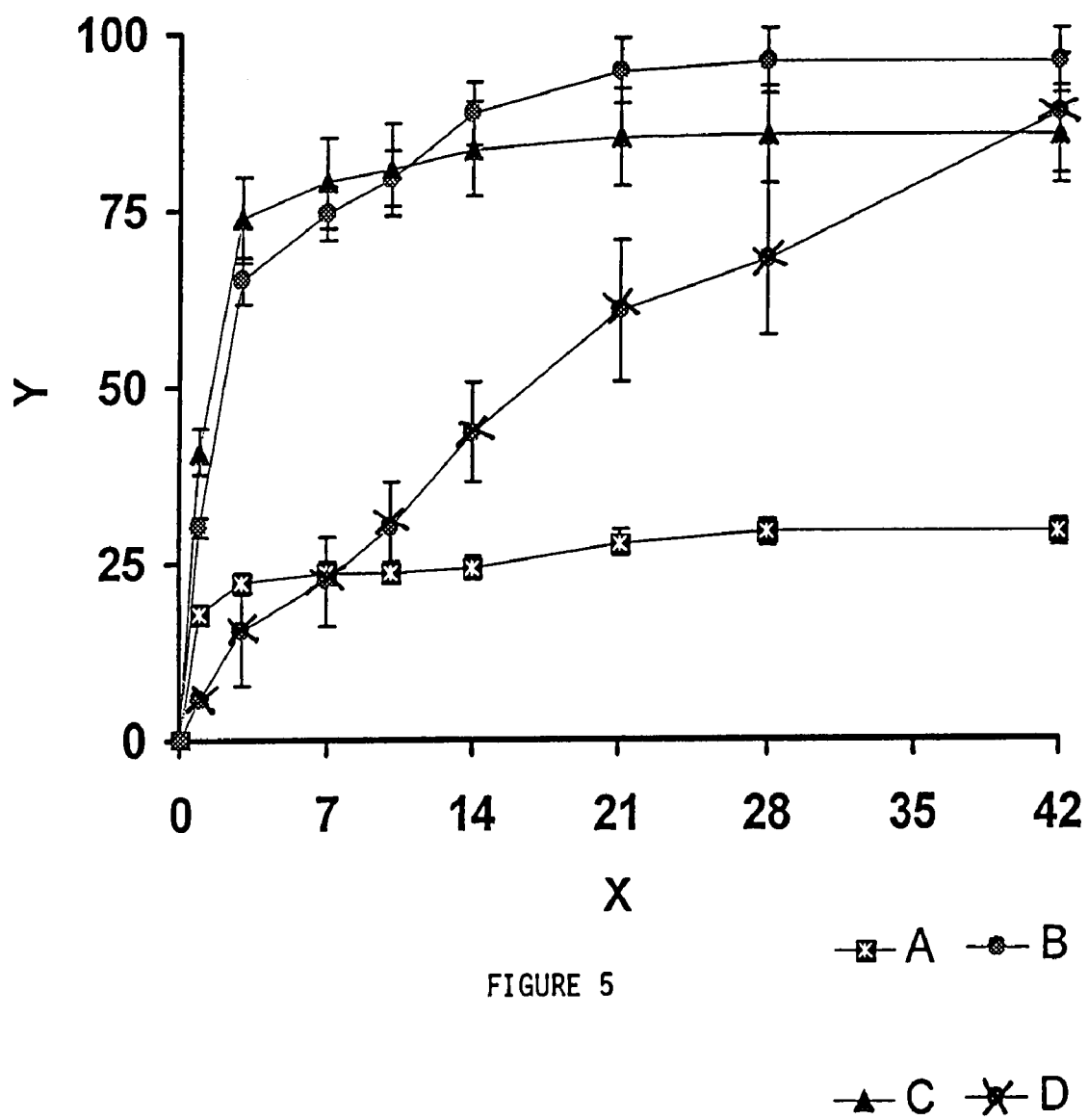
FIG. 5 is a graph illustrating the controlled release of protein from PLGA microparticles over a period of 42 days

The present invention is directed towards a controlled release formulation that releases a protein with a selected initial burst and at a selected rate over a period of several weeks or months. Typically, the initial burst is controlled to a selected value or is minimized while the release rate over period of time is controlled to be substantially linear. The invention further comprises of a biologically effective amount of a protein and a stabilizing effective amount of a polysaccharide gum material encapsulated in a biodegradable polymer such as PLGA. Protein in this composition is selected from the group consisting of an enzyme, an antibody, a hormone, a growth factor, or a cytokine wherein said gum is selected from the group consisting of gum arabic, guar gum, xanthan gum, locust bean gum, gum karaya, gum ghatti, and tragacanth gum.

As used herein the term "biologically active protein" includes proteins and polypeptides that are administered to patients as the active drug substance for prevention of or treatment of a disease or condition as well as proteins and polypeptides that are used for diagnostic purposes, such as enzymes used in diagnostic tests or in in vitro assays as well as proteins that are administered to a patient to prevent a disease such as a vaccine. Contemplated for use in the compositions of the invention are therapeutic proteins and polypeptides such as enzymes, e.g., glucocerebrosidase, adenosine deaminase; antibodies, e.g., Herceptin® (trastuzumab), Orthoclone OKT®3 (muromonab-CD3); hormones, e.g., insulin and human growth hormone (HGH); growth factors, e.g., fibroblast growth factor (FGF), nerve growth factor (NGF), human growth hormone releasing factor (HGHRF), and cytokines, e.g., leukemia inhibitory factor (LIF), granulocyte-colony stimulating factor (G-CSF), granulocyte macrophage-colony stimulating factor (GM-CSF), interleukin-6 (IL-6), interleukin-11 (IL-11), interleukin-9 (IL-9), oncostatin-M (OSM), and ciliary neurotrophic factor (CNTF).

Additional acronyms used herein:
BSA=bovine serum albumin
BTEE=benzoyl-L-tyrosine ethyl ester;
CT=chymotrypsin;
CTAB=cetyltrimethyl ammonium bromide;
DMSO=dimethyl sulfoxide;
DOTAP=N-(1-[2,3-Dioleoyloxy]propyl)-N,N,N-trimethylammonium;

FITC=fluorescein isothiocyanate;
FITC-CT=chymotrypsin with fluorescein isothiocyanate;
GACT=gum arabic and chymotrypsin;
HSA=human serum albumen
PBS=phosphate buffered saline
PCDP=L-α-phosphatidyl choline, dipalmitoyl;
PLGA=poly(lactic-co-glycolic) acid; and
PVP=polyvinylpyrollidone.

The term "pharmaceutically effective amount" refers to that amount of a therapeutic protein having a therapeutically relevant effect on a disease or condition to be treated. A therapeutically relevant effect relieves to some extent one or more symptoms of a disease or condition in a patient or returns to normal either partially or completely one or more physiological or biochemical parameters associated with or causative of the disease or condition. Specific details of the dosage of a particular active protein drug may be found in the drug labeling, i.e., the package insert (see 21 CFR § 201.56 & 201.57) approved by the United States Food and Drug Administration. The details of the present invention disclosed herein will allow those skilled in the art to adjust the initial burst and rate of release to achieve a desired therapeutic effect by delivering a pharmaceutically effective amount to match a particular disease state.

Therapeutic agent refers to the protein that is stabilized and is typically active when administered in pharmaceutically effective amounts to produce a therapeutically relevant effect. In some embodiments of the invention one or more therapeutic agents (a mixture of proteins) may be used. In other embodiments, other therapeutic agents (other than proteins) may be mixed with the protein and stabilizer so as to administered therewith and produce enhanced therapeutic effects.

Polysaccharide gums are natural products typically extracted from various plants, trees and bacteria, such as *Cyamopsis tetragonolobus* (guar gum) and *Ceratonia siliqua* (locust bean or carob gum) and *Astragalus gummifer* (tragacanth) from plants of the Leguminosae family; gum arabic and tamarind gum from respectively the *Acacia senegal* tree and *Tamarindus indica* tree; xanthan gum from the bacterial genus *Xanthamonas campestris* gum ghatti from *Anogeissus latifolia* and gum karaya from *Sterculia urens*. Many grades and forms of polysaccharide gums are commercially available. While polysaccharide gums derived from natural sources are preferred in the present invention, synthetic or modified polysaccharide gums that exhibit selected useful properties of the naturally derived gums are also useful with the invention.

The gum arabic used in the solutions of the invention had a highly branched galactose core with linkages to other sugars and contains about 1% glycoprotein; the locust gum used herein had a mannan chain (1 carbon to 4 carbon position link) with galactose substituted at the 6-position of about 20% of the mannose units; the guar gum used herein had a mannan chain (1 carbon to 4 carbon position link) with galactose substituted at the 6- position of about 40% of the mannose units; and the xanthan gum used herein had a glucan chain (1 carbon to 4 carbon position link) with trisaccharides substituted on about every other glucose.

According to the preferred embodiment of the present invention, increasing concentrations of high molecular weight polysaccharide gums (i.e., greater than 200K Daltons) are typically utilized for effective protein stabilization. The polysaccharide gums described herein are more effective protein stabilizers than commonly used small molecule protein stabilizers such as monosaccharides, disaccharides, and detergents. High molecular weight, branched chain or substituted polysaccharides such as gum arabic, guar gum, xanthan gum, locust bean gum, tragacanth gum, gum karaya and gum ghatti are more effective protein stabilizers than linear chain polysaccharides such as cellulose, agarose, xylan, konjak, or chitosan.

Polysaccharide gums are hydrogels that can absorb many times their weight of water. Therefore, it is preferable to restrict the tendency of the gums to swell in order to maintain the high polysaccharide concentrations that effectively stabilize proteins. The high gum concentration can be maintained by enclosing the gels in a biodegradable polymer such as poly(lactic-co-glycolic acid) microparticle. The particles then can be injected or implanted into a patient or test subject for the controlled release of stabilized protein over extended periods. Over time, the protein is steadily released from the particle in an active form by the hydrolysis or degradation of the biodegradable polymer.

The present invention includes polysaccharide gums that are incorporated into drug delivery devices for the purposes of (i) stabilizing proteins and (ii) controlling the rate at which the proteins diffuse from the delivery device. The polysaccharide gums of the present invention stabilize native protein conformations, even at high protein concentrations. Thus, the delivery device can be loaded with a protein/gum composition that contains a high concentration of protein, or with a mixture in the solid form, thereby increasing the drug load of the device.

The stabilized protein solutions of the invention may contain minor amounts (from about 0.5% to about 5.0% W/V) of auxiliaries and/or excipients, such as N-acetyl-dl-tryptophan, caprylate, acetate, citrate, glucose and electrolytes, such as the chlorides, phosphates and bicarbonates of sodium, potassium, calcium and magnesium. They can furthermore contain: acids, bases or buffer substances for adjusting the pH, salts, sugars or polyhydric alcohols for isotonicity and adjustment, preservatives, such as benzyl alcohol or chlorobutanol, and antioxidants, such as sulphites, acetylcysteine, Vitamin E or ascorbic acid.

Suitable tonicity adjustment agents may be, for instance, physiologically acceptable inorganic chlorides, e.g. sodium chloride; sugars such as dextrose; lactose; mannitol; sorbitol and the like. Preservatives suitable for physiological administration may be, for instance, esters of parahydroxybenzoic acid (e.g., methyl, ethyl, propyl and butyl esters, or mixtures of them), chlorocresol and the like.

The pH of the solution can be adjusted using a physiologically acceptable acid e.g. an inorganic mineral acid such as hydrochloric, hydrobromic, sulfuric, phosphoric, nitric and the like, or an organic acid such as acetic, succinic, tartaric, ascorbic, citric, glutamic, benzoic, methanesulphonic, ethanesulfonic and the like, or a physiologically acceptable base, such as sodium hydroxide, potassium hydroxide, calcium hydroxide, magnesium hydroxide and the like, an physiologically acceptable buffer solution, e.g., a chloride buffer, an acetate buffer, a phosphate buffer and the like.

Gum arabic, an anionic polysaccharide, was found to be a very effective stabilizer for proteins under physiological conditions. Spray drying a gum arabic solution containing an enzyme, chymotrypsin, resulted in hydrophilic, 1–5 μm sized particles that were negatively charged. Encapsulating such charged hydrophilic particles in hydrophobic PLGA polymer resulted in low encapsulation and rapid burst of proteins. In order to overcome this problem, the negatively charged hydrophilic particles were coated with a positively charged surfactant. This resulted in a hydrophobic coating that allowed better encapsulation within PLGA.

According to the present invention, a preferred method for stabilizing a therapeutic protein in a drug delivery system comprises the steps of (a) providing a protein as an aqueous solution; (b) adding an aqueous polysaccharide gum to the protein; (c) spray drying or lyophilizing said polysaccharide gum and protein solution to yield dry particles under conditions wherein the protein retains enzymatic activity; (d) coating said polysaccharide gum and protein particles with a surfactant; and (e) encapsulating said coated particles within a biodegradable polymer such as PLGA.

The polysaccharide gum is selected based on its ability to both stabilize the protein and control the protein's rate of release. In some embodiments, single or multiple gums and single or multiple mixtures of gums can be used in the microparticle.

Other polymers that are biodegradable polymers other than the PLGA discussed herein may be used with the invention. Typical polymers include hydrophobic bioabsorbable polymers such as polyglycolide, polylactide (D, L, DL), polydioxanones, polyestercarbonates, polyhydroxyalkonates, polycaprolactone (polylactones), polyethylene glycol, mixtures thereof, and copolymers made from two or more precursors of the above. The most preferable polymers are polyglycolide or polylactide, or copolymers selected from two or more precursors of polyglycolide, polycaprolactone, or polylactide.

Referring now to FIG. 1, this figure is a schematic diagram illustrating typical steps in the production of the microparticles according to the invention. Typically, a stabilizer 101 is mixed with a protein 103 to produce a matrix of protein and stabilizer that results in a stabilized protein 105. In one embodiment the stabilizer 101 and protein 103 are oppositely charged e a stable stabilized protein 105. Thus the stabilizer 101 may be negatively charged and the protein 103 positively charged and vice versa. In yet another embodiment the stabilizer 101 may be uncharged. Depending on the relative charges of the stabilizer 101 and the protein 103 the resulting stabilized protein 105 typically has a net positive or negative charge. Thus either anionic or cationic surfactants may be used with the invention depending on the net charge on the stabilized protein 105.

The stabilized protein complex 105 is then further reacted with a surfactant 107 to coat the surface of the stabilized protein complex with the surfactant 107. Typically the surfactant 107 aligns itself so that when the net charge of the protein complex is negative the positive end of the surfactant is attracted to the protein complex 105 and vice versa. Typically, a second intermediate product formed is a surfactant coated stabilized protein 109. Typically one or more of surfactant coated stabilized protein 109 particles are then further processed with an encapsulant 111 to form a microparticle 113.

In another embodiment, one or more stabilized protein 105 matrices is further processed with an encapsulent 111 (without first reacting with a surfactant) to produce a stabilized coated microparticle (not shown).

Referring now to FIG. 2, this figure shows the results of a scanned electron micrograph of stabilized microparticles according one embodiment of the invention where surfactants 107 are not used. The stabilized microparticles consist of stabilizer 101 mixed with protein 103, and encapsulated in an encapsulant 111 (PLGA). The upper left hand corner shows the dimensions of a stabilized microparticle of about 4.67 μm. Typically the microparticles have a particle size range of about 1 to 25 μm. Particle size and particle size distribution may be influenced by adjustment of reaction conditions.

Referring now to FIG. 3, this figure shows a scanned electron micrograph of the microparticles containing the stabilizer (101) mixed with protein (103) coated with surfactant (CTAB) (107) and encapsulated in PLGA (111). The upper left hand corner shows the dimensions of a typical stabilized microparticle to be about 5 μm. Typically the microparticles have a particle size range of about 1 to 150 μm. Preferably the microparticles have a particle size range of about 5 to 50 μm. Particle size and particle size distribution may be influenced by adjustment of reaction conditions.

Referring now to FIG. 4, this figure is a graph that shows the initial burst from microparticles containing stabilizer (gum arabic) and protein particles (CT) coated with different surfactants and encapsulated in PLGA:

(1) and (2) stabilizer and 50 mM CTAB surfactant;

(3) and (4) stabilizer and 50 mM DOTAP surfactant;

(5) no stabilizer, 50 mM CTAB surfactant;

(6) no stabilizer, 50 mM DOTAP surfactant;

(7) no stabilizer, no surfactant;

(8) stabilizer no surfactant.

The axis are calibrated as follows, X=various formulations (1) through (8) above; Y=% cumulative release of protein in 24 hrs into phosphate buffered saline, pH 7.4. It is readily apparent that the positively charged surfactants in the presence of the negatively charged stabilizer decrease the initial burst substantially.

Referring now to FIG. 5, this figure is a graph illustrating the controlled release of protein (CT) from PLGA microparticles over a period of 42 days. The axis X is calibrated in days and the axis Y is calibrated in % cumulative release. Formulation (A) contains protein (CT) and surfactant (CTAB); (B) contains protein (CT) alone; (C) contains protein (CT) and stabilizer (gum arabic); (D) contains protein (CT), stabilizer (gum arabic) and surfactant (CTAB). All formulations are encapsulated in 75:25 PLGA polymer.

Referring now to FIG. 6, this figure is a graph illustrating the controlled release of chymotrypsin from PLGA microparticles over 28 days in the presence of gum arabic and the cationic surfactant, DOTAP. The X axis is calibrated as time in days and the Y axis is calibrated in % cumulative release. All formulations are encapsulated in 75:25 PLGA polymer.

The following examples illustrate the effectiveness of the compositions and methods of the present invention in stabilizing proteins under different environmental conditions and in different model delivery systems. The examples are merely illustrative of the invention and are not intended to limit the scope of the invention.

EXAMPLE 1

This example illustrates the labeling of chymotrypsin with fluorescein isothiocyanate (FITC-CT). Chymotrypsin (CT, 10 mg) was dissolved in 10 mL of 0.1M carbonate-bicarbonate buffer (pH 9.41). A vial containing 10 mgs of fluorescein isothiocyanate (FITC) was dissolved in 1 mL of dimethyl sulfoxide (DMSO) and added to the CT solution. All reactions were carried out in the dark to prevent photo bleaching of FITC. The reaction mixture was stirred for 1 hour at room temperature and 1 mL of ethanolamine was added. Further stirring at room temperature for 1 hour was carried out in the dark and the reaction mixture was dialyzed against 1 L double distilled water using a 10K Dalton molecular weight cut off membrane. Dialysis was carried out thrice at 4° C. for 8 hours each time. The sample was then frozen and lyophilized overnight to give an orange colored powder.

The stability of the FITC-CT particles was evaluated as given in Example 14.

EXAMPLE 2

This example illustrates the encapsulation of gum arabic and chymotrypsin in PLGA in the presence of Tween-80™ using a water-in-oil-in-water double emulsion method. Protein loaded polymer microparticles were made using a modified double emulsion method. A 10% polymer solution was made by dissolving 250 mg of poly(lactic-co-glycolic) acid (PLGA, 75:25) in 2.5 ml of methylene chloride. Five mg of FITC-CT (Example 1) and 5 mg chymotrypsin were added into 2 ml phosphate buffer (no salt, pH 7.5) and stirred in the dark. This solution was added to 50 mg of gum arabic and 25 µL of Tween-80™ was added to this gum arabic and chymotrypsin solution. The mixture was homogenized on ice for 1 minute and kept on ice for 5 minutes to settle. The polymer solution containing gum arabic, chymotrypsin and Tween-80™ was added to 2.5 ml PLGA solution and sonicated twice on ice for 30 seconds each time. This resulted in a first water-in-oil emulsion. One hundred ml of 1% polyvinylpyrollidone made in 10 mM phosphate buffered saline (1% PVP/PBS) was added drop-wise to the first emulsion and homogenized on ice using a Polytron™ turrax for 10 min. This resulted in the water-in-oil-in-water second emulsion step. The solution was removed from ice and stirred at room temperature for 20 minutes. An additional 60 ml of 1% PVP/PBS was added drop-wise and the resulting solution was stirred overnight at room temperature. Microparticles that were generated during this process were filtered using a 0.22 µm filter and washed twice with 20 ml double distilled water each time. The supernatant was collected and protein content was estimated using fluorescence as given in Example 12. The particles that were collected were later freeze-dried overnight to give free flowing powder.

EXAMPLE 3A

This example illustrates the preparation of spray dried chymotrypsin particles. Chymotrypsin (50 mg) and FITC-CT (50 mg) were dissolved in 10 mL of 10 mM phosphate buffer (pH 7.4, no salt). The enzyme solution was spray dried on a bench top Buchi-191™ spray dryer using the following parameters: inlet temperature of about 100° C.; outlet temperature of about 60° C.; N₂ inlet 800 Nl/h; aspirator set at 100%; pressure of −50 mbar; and a flow rate of 6%. Powder was collected into a glass vial and dried in vacuum for a couple of hours. The particles generated were visualized under a con-focal microscope and the size was found to be about 1 um.

The stability of the spray dried chymotrypsin particles was evaluated as given in Example 14.

EXAMPLE 3B

This example illustrates the preparation of spray dried gum arabic plus chymotrypsin particles. Gum arabic (500 mg) was dissolved in 100 ml of 10 mM phosphate buffer (no salt) and the pH was adjusted to 7.4 using 4M NaOH. Chymotrypsin (50 mg) and FITC-CT (50 mg) were added to the gum arabic solution and homogenized on ice. The solution was let to stand on ice for 10 minutes before spray drying. The reaction mixture containing gum arabic and chymotrypsin was spray dried using the following parameters: inlet temperature of about 100° C.; outlet temperature of about 60° C.; N₂ inlet 800 Nl/h; aspirator set at 100%, pressure of −50 mbars; and a flow rate of 6%. Powder was collected into a glass vial and dried in vacuum for couple of hours. The particles generated were visualized under a con-focal microscope and the size was found to be about 1 um.

The stability of the spray dried gum arabic and chymotrypsin particles was evaluated as given in Example 14.

EXAMPLES 4A & 4B

These examples illustrate the encapsulation of spray dried chymotrypsin in PLGA using a solid-in-oil-in-water emulsion method.

EXAMPLE 4A

A 20% polymer solution was made by dissolving 500 mg of PLGA in 2.5 mL methylene chloride. Ten mg of the chymotrypsin particles generated by spray drying in Example 3A were suspended in the polymer solution and sonicated on ice for 30 seconds. This gave a solid in oil first emulsion. The first emulsion was added to 1 ml of methylene chloride and stirred end-over-end for 10 minutes. The emulsion was then added drop-wise to an Erlenmeyer flask containing 100 ml of 1% PVP/PBS and homogenized on ice for 10 minutes. This formed a solid-in-oil-in-water second emulsion. The second emulsion was then homogenized in a water bath at 37° C. for 1 hour. Particles sticking to the sides of the flask are intermittently scraped and an additional 100 mL 1% PVP/PBS was added after 60 minutes. The resultant suspension was further homogenized at 37° C. for an hour and filtered through a 0.22 µm sterile filter. The supernatant was collected and protein content was estimated using fluorescence as given in Example 12. The particles were washed twice in double distilled water and lyophilized to give a free-flowing powder.

EXAMPLE 4B

A 10% polymer solution was made by dissolving 250 mg of PLGA in 2.5 mL methylene chloride. Encapsulation of spray-dried chymotrypsin in the 10% PLGA solution was carried out using the protocol or Example 4A.

EXAMPLES 5A AND 5B

These examples illustrate the encapsulation of spray dried gum arabic and chymotrypsin particles in PLGA using a solid-in-oil-in-water emulsion method.

EXAMPLE 5A

A 20% polymer solution was made by dissolving 500 mg of PLGA in 2.5 mL methylene chloride. Sixty mg of the gum arabic-chymotrypsin particles generated by spray drying in Example 3B were suspended in the polymer solution and sonicated on ice for 30 seconds. This gave a solid in oil first emulsion. This emulsion was added to 1 ml of methylene chloride and stirred end-over-end for 10 minutes. The emulsion was then added drop-wise to an Erlenmeyer flask containing 100 ml of 1% PVP/PBS and homogenized on ice for 10 minutes. This formed a solid-in-oil-in-water second emulsion. The second emulsion was then homogenized in a water bath at 37° C. for 1 hour. Particles sticking to the sides of the flask are intermittently scraped and an additional 100 mL 1% PVP/PBS was added after 60 minutes. The resultant suspension was further homogenized at 37° C. for an hour and filtered through a 0.22 µm sterile filter. The supernatant was collected and protein content was estimated using fluorescence as given in Example 12. The collected particles were washed twice in double distilled water and lyophilized to give a free-flowing powder.

EXAMPLE 5B

A 10% polymer solution was made by dissolving 250 mg of PLGA in 2.5 mL methylene chloride. Encapsulation of the spray-dried gum arabic and chymotrypsin in the 10% PLGA solution was carried out using the protocol of Example 5A.

EXAMPLE 6

This example illustrates the encapsulation of spray dried chymotrypsin particles in PLGA coated with a cationic hydrophobic surfactant (CTAB), using a solid-in-oil-in-water emulsion method. A 20% polymer solution was made by dissolving 500 mg of PLGA in 2.5 mL methylene chloride. Ten mg of the chymotrypsin particles generated by spray drying in Example 3A were suspended in the polymer solution and sonicated on ice for 30 seconds. This gave a solid in oil first emulsion. This emulsion was added to 1 of methylene chloride containing 18 mg of cetyltrimethylammonium bromide surfactant (CTAB, 50 mM) and stirred end-over-end for 10 minutes. The emulsion was then added drop-wise to an Erlenmeyer flask containing 100 ml of 1% PVP/PBS and homogenized on ice for 10 minutes. This formed the solid-in-oil-in-water second emulsion. This emulsion was then homogenized in a water bath at 37° C. for 1 hour. Particles sticking to the sides of the flask are intermittently scraped and an additional 100 mL 1% PVP/PBS was added after 60 minutes. The resultant suspension was further homogenized at 37° C. for an hour and filtered through a 0.22 µm sterile filter. The supernatant was collected and protein content was estimated using fluorescence as given in Example 12. The collected particles were washed twice in double distilled water and lyophilized to give a free-flowing powder.

EXAMPLE 7

This example illustrates the encapsulation of spray dried gum arabic and chymotrypsin particles in PLGA coated with a cationic hydrophobic surfactant (CTAB), in methylene chloride using a solid-in-oil-in-water emulsion method. A 20% polymer solution was made by dissolving 500 mg of PLGA in 2.5 mL methylene chloride. Sixty mg of the gum arabic-chymotrypsin particles generated by spray drying in Example 3B were suspended in 1 ml of methylene chloride containing 18 mg of cetyltrimethylammonium bromide (CTAB, 50 mM) and stirred end-over-end for 10 minutes. This gave a first solid-in-oil emulsion. The first solid-in-oil emulsion was then added drop-wise to 500 mg of 75:25 PLGA in 2.5 mL methylene chloride and sonicated for 30 seconds. This was then added to an Erlenmeyer flask containing 100 ml of 1% PVP/PBS and homogenized on ice for 10 minutes. This formed the solid-in-oil-in-water second emulsion. The solid-in-oil-in-water second emulsion was then homogenized in a water bath at 37° C. for 1 hour. Particles sticking to the sides of the flask are intermittently scraped and an additional 100 mL 1% PVP/PBS was added after 60 minutes. The resultant suspension was further homogenized at 37° C. for an hour and filtered through a 0.22 µm sterile filter. The supernatant was collected and protein content was estimated using fluorescence as given in Example 12. The collected particles were washed twice in double distilled water and lyophilized to give a free-flowing powder.

EXAMPLE 8

This example illustrates the encapsulation of spray dried gum arabic and chymotrypsin particles in PLGA coated with a cationic hydrophobic surfactant (CTAB), in ethanol using a solid-in-oil-in-water emulsion method. A 20% polymer solution was made by dissolving 500 mg of PLGA in 2.5 mL methylene chloride. Sixty mg of the gum arabic-chymotrypsin particles generated by spray drying in Example 3B were suspended in 1 ml of ethanol containing 18 mg of cetyltrimethylammonium bromide (CTAB, 50 mM) and stirred end-over-end for 10 minutes. This was centrifuged on a desktop centrifuge at 14,000 rpm for 5 minutes and ethanol removed. To this solid a 2.5 mL methylene chloride solution containing 500 mg of 75:25 PLGA was added and sonicated for 30 seconds. This gave the first solid-in-oil emulsion. This emulsion was added to an Erlenmeyer flask containing 100 ml of 1% PVP/PBS and homogenized on ice for 10 min. This forms the solid-in-oil-in-water second emulsion. The solid-in-oil-in-water second emulsion was then homogenized in a water bath at 37° C. for 1 hour. Particles sticking to the sides of the flask are intermittently scraped and an additional 100 mL 1% PVP/PBS was added after 60 minutes. The resultant suspension was further homogenized at 37° C. for an hour and filtered through a 0.22 µm sterile filter. The supernatant was collected and protein content was estimated using fluorescence as given in Example 12. The collected particles were washed twice in double distilled water and lyophilized to give a free-flowing powder.

EXAMPLE 9

This example illustrates the encapsulation of spray dried gum arabic and chymotrypsin particles in PLGA coated with a cationic hydrophobic surfactant, DOTAP, in methylene chloride using a solid-in-oil-in-water emulsion method. A 20% polymer solution was made by dissolving 500 mg of PLGA in 2.5 mL methylene chloride. Sixty mg of the gum arabic-chymotrypsin particles generated by spray drying in Example 3B were suspended in 1 ml of methylene chloride containing 35 mg of N-(1-[2,3-Dioleoyloxy]propyl)N,N,N-trimethylammonium chloride (DOTAP, 50 mM) and stirred end-over-end for 10 minutes. This gave the first solid-in-oil emulsion. The emulsion was then added drop-wise to 500 mg of 75:25 PLGA in 2.5 mL methylene chloride and sonicated for 30 seconds. This was then added to an Erlenmeyer flask containing 100 ml of 1% PVP/PBS and homogenized on ice for 10 minutes. This formed the solid-in-oil-in-water second emulsion. The solid-in-oil-in-water second emulsion was then homogenized in a water bath at 37° C. for 1 hour. Particles sticking to the sides of the flask are intermittently scraped and an additional 100 mL 1% PVP/PBS was added after 60 minutes. The resultant suspension was further homogenized at 37° C. for an hour and filtered through a 0.22 µm sterile filter. The supernatant was collected and protein content was estimated using fluorescence as given in Example 12. The collected particles were washed twice in double distilled water and lyophilized to give a free-flowing powder.

EXAMPLE 10

This example illustrates the encapsulation of spray dried gum arabic and chymotrypsin particles in PLGA coated with a cationic hydrophobic surfactant (DOTAP), in methylene chloride using a solid-in-oil-in-water emulsion method. A 20% polymer solution was made by dissolving 500 mg of PLGA in 2.5 mL methylene chloride. Sixty mg of the gum arabic-chymotrypsin particles generated by spray drying in Example 3B were suspended in 1 ml of methylene chloride containing 3.5 mg of N-(1-[2,3-Dioleoyloxy]propyl)N,N,N-trimethylammonium chloride (DOTAP, 5 mM) and stirred end-over-end for 10 minutes. This gave a first solid-in-oil emulsion. The emulsion was then added drop-wise to 500 mg of 75:25 PLGA in 2.5 mL methylene chloride and sonicated for 30 seconds. This was then added to an Erlenmeyer flask containing 100 ml of 1% PVP/PBS and homogenized on ice for 10 minutes. This formed a solid-in-oil-in-water second emulsion. The solid-in-oil-in-water second emulsion was then homogenized in a water bath at 37° C. for 1 hour. Particles sticking to the sides of the flask are intermittently scraped and an additional 100 mL 1% PVP/PBS was added after 60 minutes. The resultant suspension was further homogenized at 37° C. for an hour and filtered through a 0.22 μm sterile filter. The supernatant was collected and protein content was estimated using fluorescence as given in Example 12. The collected particles were washed twice in double distilled water and lyophilized to give a free-flowing powder.

EXAMPLE 11

This example illustrates the encapsulation of spray dried gum arabic and chymotrypsin particles in PLGA coated with a zwitter-ionic hydrophobic surfactant, PCDP, using a solid-in-oil-in-water emulsion method. A 20% polymer solution was made by dissolving 500 mg of PLGA in 2.5 mL methylene chloride. Sixty mg of the gum arabic-chymotrypsin particles generated by spray drying in Example 3B were suspended in 1 ml of methylene chloride containing 36.7 mg of L-α-phosphatidyl choline, dipalmitoyl (PCDP, 50 mM) and stirred end-over-end for 30 minutes. This gave a first solid-in-oil emulsion. The first emulsion was added drop-wise to 500 mg of 75:25 PLGA in 2.5 mL methylene chloride and sonicated for 30 seconds This was then added to an Erlenmeyer flask containing 100 ml of 1% PVP/PBS and homogenized on ice for 10 minutes. This formed a solid-in-oil-in-water second emulsion. This second emulsion was then homogenized in a water bath at 37° C. for 1 hour. Particles sticking to the sides of the flask are intermittently scraped and an additional 100 mL 1% PVP/PBS was added after 60 minutes. The resultant suspension was further homogenized at 37° C. for an hour and filtered through a 0.22 μm sterile filter. The supernatant was collected and protein content was estimated using fluorescence as given in Example 12. The collected particles were washed twice in double distilled water and lyophilized to give a free-flowing powder.

EXAMPLE 12

This example illustrates the estimation of protein content in the supernatant. A 100 μl aliquot of the supernatant that was collected after each PLGA microparticle synthesis was added to 900 μL of 1 M Tris-HCl, pH 7.6. The solution was mixed and 250 μL was used for fluorescence analysis using a Victor™ fluorometer. A standard curve was generated by making a solution of 1 mg/mL FITC-CT in 1% PVP/PBS (in 10 mM PBS) and diluting it appropriately in 1 M Tris, pH 7.6. The fluorescence spectrum of flourescein was measured with an excitation wavelength of 490 nm and emission maxima at 520 nm.

EXAMPLE 13

This example illustrates the estimation of protein content in PLGA particles. Five mg of various particles generated using the emulsion method were treated with 1 mL of 1 M NaOH for 1 hour at 37° C. Centrifugation was carried out at 14,000 rpm for 5 minutes on a desktop and the supernatant was aliquoted. An additional 1 mL of 1M NaOH was added and the incubation process repeated for an additional hour. After centrifugation, the supernatants were mixed. Fifty μL of the 2 mL NaOH supernatant solution was added to 200 μL of 1 M Tris-HCl, pH 7.6 and fluorescence spectrum of fluorescein was measured (Excitation=490 nm; Emission=520 nm) using a Victor™ fluorometer. A standard curve was generated by incubating a 1 mg/mL solution of FITC-CT under similar conditions.

EXAMPLE 14

This example illustrates a chymotrypsin stability and activity assay. Enzyme activity was measured by the hydrolysis of benzoyl-L-tyrosine ethyl ester (BTEE). Chymotrypsin activity assays were typically carried out at 25° C. using a micro titer plate reader. Typically, chymotrypsin at a concentration of 0.05 mg/ml was assayed with 1.54 mM BTEE in 0.04 M Tris (pH 7.8) and 0.05M $CaCl_2$. The increase in absorbance at 256 nm was monitored over 5–15 minutes and the linear portion of the curve was used to determine reaction velocity. Freshly prepared chymotrypsin was used as a control and the other formulations were compared to this. Results from activity assays for chymotrypsin, FITC-chymotrypsin, spray dried chymotrypsin and spray dried gum arabic/chymotrypsin are given in Table 3.

TABLE 1

Percentage encapsulation and initial burst release of chymotrypsin in PLGA microspheres.

| Formulations | % Protein Encapsulation | % Initial burst (24 hour) |
| --- | --- | --- |
| Example 2 | 10 ± 2 | ND |
| Example 4A | 10 ± 5 | 29 ± 2 |
| Example 5 | 30 ± 10 | 39 ± 2 |
| Example 6 | 30 ± 5 | 18 ± 3 |
| Example 7 | 70 ± 10 | 5 ± 1 |
| Example 9 | 93 ± 1 | 5 ± 1 |
| Example 10 | 55 ± 5 | 13 ± 4 |
| Example 11 | 20 ± 2* | ND |

*Determined in duplicate in only one experiment;
ND = not determined

As can be seen in Table 1, protein encapsulation in the PLGA microspheres was highest when both gum arabic and a 50 mM cationic detergent (CTAB or DOTAP) were used (Examples 7 and 9). Additionally the combination of the gum, detergent and the protein in the PLGA microparticles reduces the amount of protein that is released during initial burst, that is, within 24 hours. Examples 7 and 9 released about 5% of the encapsulated protein in the initial burst, which was about a substantially lower than that released by other formulations. When the protein was encapsulated only in the presence or absence of gum arabic the percentage protein released during the initial burst was higher (about 30%).

TABLE 2

Controlled release of chymotrypsin from PLGA microspheres over 6 weeks in PBS, pH 7.4

| Formulations | % Released in 1 week | % Released in 2 weeks | % Released in 4 weeks | % Released in 6 weeks |
|---|---|---|---|---|
| Example 4A | 74 ± 3 | 88 ± 5 | 96 ± 3 | 96 ± 3 |
| Example 5 | 78 ± 6 | 83 ± 4 | 85 ± 6 | 85 ± 6 |
| Example 6 | 23 ± 3 | 24 ± 1 | 29 ± 4 | 29 ± 4 |
| Example 7 | 22 ± 6 | 43 ± 7 | 68 ± 6 | 90 ± 6 |
| Example 9 | 13 ± 1 | 24 ± 2 | 29 ± 2 | ND |
| Example 10 | 36 ± 6 | 46 ± 8 | 60 ± 6 | ND |

ND = not determined

As seen in Table 2, chymotrypsin release from PLGA microspheres depended on the formulation. Protein formulations without the aid of either gum arabic or the cationic detergent (Example 4A) released substantial amount of protein within the first week of incubation (about 74% of encapsulated protein), protein formulations with gum arabic (Example 5) but without the cationic detergent coating also released similar amount of protein (about 78%). However, protein formulations with only the cationic detergent, CTAB, (Example 6) showed low percentage release during the first week (about 23%) and negligible protein release thereafter. Coating the gum arabic and protein particle with 50 mM CTAB (Example 7), not only showed lower burst effect, but also showed a consistent and near zero order release. Almost all the protein encapsulated in the PLGA particles in this formulation was released in 42 days. Coating the gum arabic and protein particle with 50 mM of another cationic detergent, DOTAP, showed low initial burst (Example 9), however, not much protein was released in 4 weeks. Changing the formulation to a coating with 5 mM DOTAP showed an initial burst of about 13% (see Table 10), 36% released during the first week and a substantial release in 4 weeks (Example 10, about 60%).

TABLE 3

Chymotrypsin activity assay

| Formulations | % Protein based on BCA analysis | % Activity with respect to bottled material |
|---|---|---|
| CT Bottled | 100 | 100 |
| CT Spray dried | 50 ± 10 | 27 ± 5 |
| CT Spray dried in the presence of gum arabic | 92 ± 4 | 80 ± 7 |
| CT that was FITC-labeled | 70 ± 7 | 66 ± 10 |

As shown in Table 3, above, chymotrypsin lost activity (about 70%) when it was spray dried under the conditions given in the examples section. However, spray drying in the presence of gum arabic, chymotrypsin lost only around 10% activity. This indicates that the gum preserves the enzymatic activity of chymotrypsin during spray drying even under harsh conditions. Additionally, labeling chymotrypsin with FITC also led to loss of about 30% activity compared to unlabeled enzyme.

As shown in Table 4, below, chymotrypsin (CT) is stabilized by gum arabic towards sonication during particle preparation. Sonication of proteins in absence of a stabilizer led to loss of activity for several proteins including chymotrypsin. The addition of CTAB, a cationic surfactant, did not reduce the stabilization properties of the gum.

TABLE 4

The stabilization of chymotrypsin (CT) towards sonication by gum arabic

| Formulations | % Activity* with respect to CT |
|---|---|
| Spray Dried CT | 12 |
| Spray Dried CT + gum arabic | 115 |
| Spray Dried CT + gum arabic + CTAB | 129 |

*Results are average from a single experiment.
Samples were run in duplicate

Homogenization induced loss of activity of proteins is a common detrimental step encountered during particle generation. Table 5, below, demonstrates that the activity of CT is retained in the presence of gum arabic in the presence or absence of the cationic surfactant CTAB towards homogenization.

TABLE 5

The ability of gum arabic to stabilize chymotrypsin (CT) towards homogenization.

| Formulations | % Activity* with respect to CT |
|---|---|
| Spray Dried CT | 12 |
| Spray Dried CT + Gum Arabic | 82 |
| Spray Dried CT + Gum Arabic + CTAB | 112 |

*Results are average from a single experiment.
Samples were run in duplicate

The final two stages of biodegradable particle preparation are emulsification and drying of the particles. Both of these processes have rendered proteins inactive as reported in several literature articles. Table 6, below, demonstrates that gum arabic protects the enzyme activity of CT towards both of these steps in the presence or absence of the cationic surfactant, CTAB.

TABLE 6

Gum arabic stabilizes protein towards emulsification and drying

| Formulations | % Specific Activity with respect to CT* |
|---|---|
| Spray Dried CT | 17 |
| +CTAB | 22 |
| +GA | 163 |
| +GA + CTAB | 132 |

Figure 6:
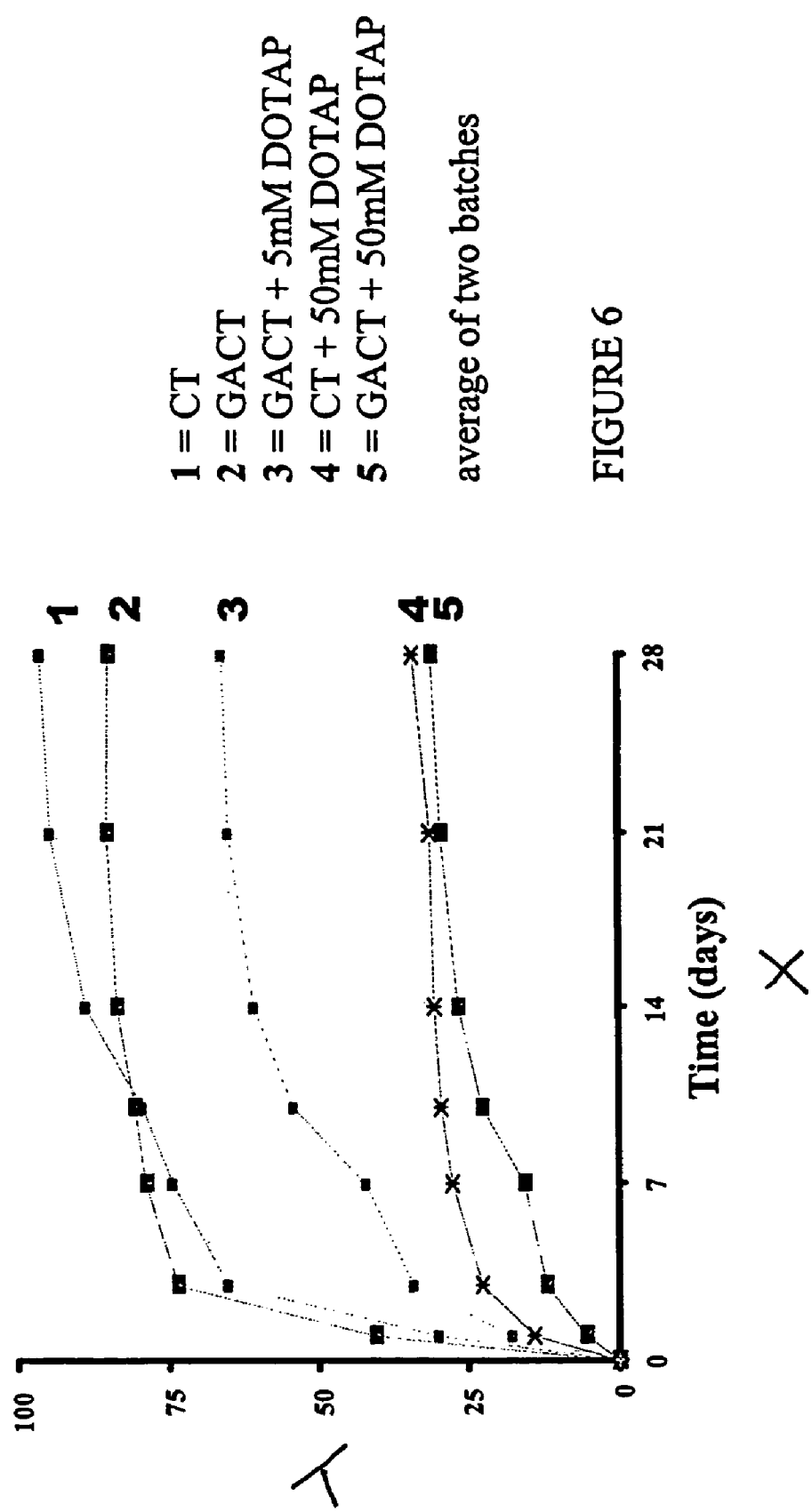
FIG. 6 is a graph illustrating the controlled release of chymotrypsin from PLGA microparticles over 28 days in the presence of gum arabic and the cationic surfactant, DOTAP.

*Results are average from a single experiment in PBS, pH 5.3.
Samples were run in duplicate The inventors have demonstrated that CTAB coated gum arabic and chymotrypsin particles have near zero order controlled release from PLGA microparticles. FIG. 6 demonstrates that particles of gum arabic and chymotrypsin coated with another cationic surfactant, DOTAP, also have controlled release properties over a period of about four weeks. This also demonstrates that depending on the surfactant, and its concentration, one can modify the release properties of the protein from PLGA microparticles.

Referring now to Table 7, the table lists data giving a depiction of the percent specific activity of a protein, chymotrypsin (CT) released from PLGA microparticles over a period of 22 days in PBS, at about pH 7.4 and at a temperature of about 37° C. The Specific Activity results are average from a single release experiment at 37° C. in a buffer containing PBS (pH 7.4), 5% GA, and 1% BSA. Samples were run in duplicate.

TABLE 7

| Formulation | Time (Days) | Specific Activity (%) |
|---|---|---|
| CT | 1 | 15 |
| CT | 8 | 3 |
| CT | 14 | 1 |
| CT | 22 | ND* |
| GACT/CTAB | 1 | 100 |
| GACT/CTAB | 8 | 78 |
| GACT/CTAB | 14 | 75 |
| GACT/CTAB | 22 | 66 |

*ND—Not Determined

While controlled release of proteins has been achieved, the stability of the released protein has been elusive in the prior art. Typically the prior art formulations release inactive proteins. Table 7 demonstrates that the microparticles containing gum arabic and the cationic surfactant (CTAB), not only control the release of the protein from PLGA microparticles, but also stabilize it prior to release over a period of at least about 3 weeks.

While the forms of the invention herein disclosed constitute presently preferred embodiments, many others are possible. It is not intended herein to mention all of the possible equivalent forms or ramifications of the invention. It is to be understood that the terms used herein are merely descriptive, rather than limiting, and that various changes may be made without departing from the spirit of the scope of the invention.

We claim:

1. A controlled release formulation comprising:
a protein mixed with a polysaccharide stabilizer comprising microparticles;
a surfactant coated on the microparticles; and
a biodegradable polymer encapsulating the surfactant coated microparticles.

2. The controlled release formulation according to claim 1, wherein the biodegradable polymer comprises homo or heteropolymers of lactic and glycolic acids.

3. The controlled release formulation according to claim 1, wherein the biodegradable polymer is a hydrophobic bioabsorbable polymer.

4. A controlled release formulation comprising:
 a. a protein;
 b. a stabilizer mixed with the protein; and
 c. a surfactant coated on the stabilizer protein mixture comprising surfactant coated microparticles; and
 d a biodegradable polymer in which the surfactant coated microparticles are encapsulated.

5. The controlled release formulation according to claim 4, wherein the stabilizer has a charge and the surfactant has a charge opposite to the stabilizer.

6. The controlled release formulation according to claim 4, wherein the stabilizer is uncharged and the surfactant is uncharged.

7. The controlled release formulation according to claim 4, wherein the stabilizer is uncharged and the surfactant is charged.

8. A controlled release formulation comprising:
 a. a protein;
 b. a stabilizer mixed with the protein wherein the protein and stabilizer mixture comprises a stabilized particle;
 c. a surfactant coated on the particle; and
 d. a biodegradable polymer encapsulating the surfactant coated particle; and
 wherein the encapsulated surfactant coated particle comprises a microparticle.

9. A method for making stabilized protein particles comprising:
 a. providing a solution of protein;
 b. providing a solution of stabilizer;
 c. mixing the solutions;
 d. generating microparticles from the mixture; and
 e. coating the microparticles with surfactant;
 f. encapsulating the surfactant coated microparticles in a biodegradable polymer.

10. The method according to claim 9, wherein the stabilized protein microparticles are suspended in an organic solvent and coated with a surfactant in an organic solvent.

11. The method according to claim 9, wherein the organic solvent is selected from the group consisting of ethanol, dichloromethane, dimethyl sulfoxide, dimethyl formamide and mixtures thereof.

12. The method according to claim 9, wherein the protein and stabilizer are mixed in a ratio of stabilizer:protein of about 500:1 to about 1:1.

13. The method according to claim 9, wherein the protein and stabilizer are mixed in a ratio of stabilizer:protein of about 10,000:1 to about 50:1.

14. The method according to claim 9, wherein when the protein comprises a therapeutic protein, the protein and stabilizer are mixed in a ratio of stabilizer:protein of about 500:200 to about 1:1.

15. The method according to claim 9, wherein when the protein comprises a therapeutic protein, the protein and stabilizer are mixed in a ratio of stabilizer:protein of about 100,000:1 to about 1:1.

16. The controlled release formulation according to claim 8, wherein the stabilizer is selected form the group consisting of polysaccharide, carrier protein, and mixtures thereof.

17. The controlled release formulation according to claim 16, wherein the polysaccharide is selected from the group of polysaccharide gums consisting of guar gum, gum arabic, gum karaya, gum ghatti, locust bean gum, tamarind gum, carageenan gum, and pectin or mixtures thereof.

18. The controlled release formulation according to claim 8, wherein when the stabilizer is a carrier protein, the stabilizer is selected from the group consisting of HSA, gelatin, BSA, and mixtures thereof.

19. The controlled release formulation according to claim 8, wherein the biodegradable polymer is a hydrophobic bioabsorbable polymer.

20. The controlled release formulation according to claim 8, wherein the biodegradable polymer is selected from the group consisting of polymers that are sensitive to environmental conditions such as temperature or pH.

21. The controlled release formulation according to claim 8, wherein the biodegradable polymer is a block copolymer of polyethylene glycol and poly (lactic-co-glycolic) acid polymers.

22. The controlled release formulation according to claim 8, wherein the biodegradable polymer is a graft copolymer of polyethylene glycol and poly (lactic-co-glycolic) acid polymer.

23. The controlled release formulation according to claim 8, wherein the particles of surfactant coated stabilized protein are dispersed within the encapsulant.

24. A method for stabilizing a protein comprising:

a. providing a protein in an aqueous solution;

b. adding an aqueous polysaccharide gum to the protein aqueous solution;

c. spray drying or lyophilizing the polysaccharide gum and protein solution to produce particles;

d. coating the polysaccharide gum and protein particles with a surfactant;

e. encapsulating the coated particles within a biodegradable polymer.

25. The controlled release formulation according to claim 3, wherein the hydrophobic bioabsorbable polymer is selected from the group consisting of polyglycolide, polylactide (D, L, DL), polydioxanones, polyestercarbonates, polyhydroxyalkanoates, polycaprolactone (polylactones), polyethylene glycol, and copolymers thereof.

26. The controlled release formulation according to claim 25, wherein the hydrophobic bioabsorbable polymer is selected from the group consisting of polyglycolide or polylactide, or a copolymer or polyglycolide-caprolactone of polyglycolide and polylactide, polylactide-polycaprolactone.

27. The controlled release formulation according to claim 19, wherein the hydrophobic bioabsorbable polymer is selected from the group consisting of polyglycolide, polylactide (D, L, DL), polydioxanones, polyestercarbonates, polyhydroxyalkanoates, polycaprolactone (polylactones), polyethylene glycol, and copolymers thereof.

* * * * *